(12) United States Patent
Amato

(10) Patent No.: US 7,560,485 B2
(45) Date of Patent: Jul. 14, 2009

(54) METHOD FOR TREATING INTERMITTENT CLAUDICATION COMPRISING THE ADMINISTRATION OF PROPIONYL L-CARNITINE AND A CONCOMITANT PHYSICAL TRAINING

(75) Inventor: Antonino Amato, North Bethesda, MD (US)

(73) Assignee: SIGMA-TAU Industrie Parmaceutiche Riunite S.p.A., Rome (IT)

( * ) Notice: Subject to any disclaimer, the term of this patent is extended or adjusted under 35 U.S.C. 154(b) by 603 days.

(21) Appl. No.: 11/242,136

(22) Filed: Oct. 4, 2005

(65) Prior Publication Data

US 2007/0078097 A1   Apr. 5, 2007

(51) Int. Cl.
*A61K 31/22* (2006.01)
(52) U.S. Cl. ..................................................... 514/546

(58) Field of Classification Search .................. 514/546
See application file for complete search history.

(56) References Cited

U.S. PATENT DOCUMENTS 5,811,457 A * 9/1998 Corsi .......................... 514/547

* cited by examiner

*Primary Examiner*—Raymond J Henley, III
(74) *Attorney, Agent, or Firm*—Nixon & Vanderhye P.C.

(57) ABSTRACT

The present invention discloses a method for treating a subject suffering from intermittent claudication (IC) wherein said subject takes an effective dose of propionyl L-carnitine or a pharmaceutically acceptable salt thereof and also engaging in a concomitant physical training program. The method is particular effective for patients with intermittent claudication at class II of the Leriche-Fontaine's classification. The method provides a relief from peripheral arterial disease symptoms, as shown by claudication-limited exercise tolerance, while also improving quality of life.

7 Claims, No Drawings

METHOD FOR TREATING INTERMITTENT CLAUDICATION COMPRISING THE ADMINISTRATION OF PROPIONYL L-CARNITINE AND A CONCOMITANT PHYSICAL TRAINING

The invention described herein relates to a method for treating intermittent claudication comprising administering an effective dosage of propionyl L-carnitine (PLC) and submitting the patient to a concomitant physical training program.

BACKGROUND OF THE INVENTION

Peripheral arterial disease (PAD) is caused by atherosclerosis of the leg arteries and is usually complicated by vascular accidents occurring not only in peripheral circulation but also in cerebral and coronary trees. Approximately one third of patients with PAD suffers from claudication, that usually deteriorates slowly: 25% of patients have worsening claudication and about 5% experience amputation within 5 years.

Patients with claudication have severe limitations in exercise capacity due to reduced blood flow in the peripheral circulation. There is evidence that impairment of carnitine function, likely as a consequence of acylcarnitine accumulation, contributes to metabolic changes that facilitate the occurrence of claudication (Hiatt, W R, et al.; *J. Clin. Invest,*. 1989; 84:1167-73).

Metabolic changes including accumulation of acyl-carnitines with eventual impairment of skeletal muscle metabolism has been reported in claudicant patients (Brass, E P; Hiatt, W R; *J. Am. Coll. Nutr.;* 1998 *Jun;* 17(3):207-15). Also, randomised placebo-controlled clinical trials with levocarnitine and propionyl L-carnitine orally given demonstrated a significant increase of walking distance in patients with claudication (Brevetti, G; et al.; *J. Am. Coll. Cardiol.;* 1995; 26:1411-6; Brevetti, G; et al.; *Eur. Heart J.;* 1992; 13:251-5; Brevetti, G; et al.; *Circulation;* 1988; 77:767-73; Brevetti, G; et al.; *J. Am. Coll. Cardiol.;* 1999; 34.1618-24; Hiatt, W R; et al.; *Am. J. Med.;* 2001; 110:616-22), suggesting a contributing role of the metabolic status in deteriorating claudication. It was demonstrated that propionyl L-carnitine inhibits arachidonic acid accumulation in the phospholipids of platelet membrane with ensuing reduction of platelet thromboxane $A_2$ and $O_2$ formation (Pignatelli, P; et al.; *Am. J. Physiol. Heart Circ. Physiol.;* 2003; 284:H41-8). A potential relevance of platelet function on the progression of PAD is known (Hiatt, W R.; *N. Engl. J. Med.;* 2001; 344:1608-1621).

Studies by Brevetti et al., see also U.S. Pat. No. 4,968,719, provide a limited teaching to the oral administration of L-carnitine or propionyl L-carnitine to a daily dose of 2 g. In particular, Brevetti et al. (*Circulation,* 1988; 77:767-73) demonstrated that, in six claudicant patients intravenously treated with 3 g L-carnitine as a bolus followed by infusion of 2 mg/Kg/man for 30 minutes, the increase of venous lactate induced by walking test was lowered; but it was not reported if this treatment had some effects on walking distance.

Corsi, U.S. Pat. No. 5,811,457, discloses the use of propionyl L-carnitine in a therapeutic method for the treatment of chronic arteriosclerosis obliterans at stage II of Leriche Fontaine's classification in patients with maximal walking distance (MWD) equal to or greater than 100 meters and shorter than 300 meters.

This reference, makes a better distinction of the patient population affected by peripheral arterial disease with respect to U.S. Pat. No. 4,968,719. The patent enables for an oral administration of 2 g/day of propionyl L-carnitine and shows that a clinical response begins to be clinically evident between the $4^{th}$ and $6^{th}$ month of treatment. The whole treatment was protracted for 12 months. The preferred administration route is the oral one and no particular weight is given to other administration routes, given as intended to be equivalent to each other.

All the studies disclosed in the prior art never gave a proper emphasis to the physical exercise of the patient jointly with PLC administration, but only used exercise performance on a treadmill as a methodologic instrument to test the efficacy of drug therapy. Physical exercise is only given as general recommendation to all claudicants in the overall advice to modify the life style. In that context, the recommendation for physical exercise is merged with other medical advices, such as stop smoking. This change in life style is expected to increase MWD.

The state of the art successfully improved the walking distance, a symptomatic parameter, and also improved the physiopathological state of the patient and the quality of life (QoL).

To date, only pharmacological clinical treatment is found effective on symptomatic improvement. Two drugs are use in clinical practice. Cilostazol (Pletal®) is the most effective and actually the most used. However, there are some concerns on its safety (www.fda.gov/cder/-news/cilostazol/approval.htm). Pentoxyfilline (Trental®) is a relatively safer drug, but far less effective and its use is limited.

In spite of all the intense search for an effective therapy for peripheral arterial disease, the need for an improved therapeutic treatment still remains, with particular view for patient's improvement of physiopathological parameters, patient's compliance (due to the treatment period length) and, finally, its safety.

Finally, symptomatic improvement is an aspect of better quality of life (QoL), which through the use of validated instruments, also assesses other realms of daily living, such as emotional status and relationship with others. Examples of validated instruments for QoL are: the Medical Outcome Scale-Short Form 36 (MOS-SF36), the Walking Impairment Questionnaire (WIQ), and others.

The ideal treatment of claudication should affect both objective symptomatic improvement (Walking Distance) and subjective functional status (QoL).

SUMMARY OF THE INVENTION

It has surprisingly been found that treating a patient suffering from intermittent claudication by administering propionyl L-carnitine and prescribing to said patient a concomitant physical training provides a relief from peripheral arterial disease symptoms, as shown by claudication-limited exercise tolerance, while also improving quality of life.

Therefore, it is an object of the present invention a method for the treatment of a patient suffering from peripheral arterial disease comprising administering to said patient an effective dose of propionyl L-carnitine or a pharmaceutically acceptable salt thereof and prescribing to said patient a concomitant physical training program during the drug treatment.

This and other objects will be disclosed in the foregoing detailed description of the invention, recurring also to examples.

DETAILED DESCRIPTION OF THE INVENTION

Propionyl L-carnitine is a well-known compound, currently available on the market or it can be easily prepared with well-known methods. The preparation of propionyl L-carnitine and its pharmaceutically acceptable salts is disclosed, for example, in the patent literature in the name of SIGMA-TAU Industrie Farmaceutiche Riunite S.p.A. Other methods are available in the non-patent literature.

Examples of pharmaceutically acceptable salts of propionyl L-carnitine are chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulfate, glucose phosphate, tartrate, acid tartrate, magnesium tartrate, 2-amino ethansulfonate, magnesium 2-amino ethansulfonate, choline tartrate and trichloroacetate.

In a preferred embodiment, the present invention is applied to patients suffering from peripheral arterial disease with a mild to severe grade. These patients belong to class II of the Leriche-Fontaine's classification as shown by an entry MWD between 70 and 890 meters, as measured on a treadmill set at 2 mph (3.2 km/h) and 7% slope.

In all cases, such patients did not suffer of rest pain (Leriche Fontaine class III). However, the medicament according to the present invention can be used advantageously in the most severe patients, in order to prevent a worsening of the disease.

Conveniently, said medicament is in the form of a preparation for oral administration, but other forms are equally suitable for carrying out the present invention. The person skilled in the art will decide the effective time of administration, depending on the patient's conditions, degree of severity of the disease, response of the patient and any other clinical parameter within the general knowledge of this matter.

The dose of propionyl L-carnitine ranges from about 1 to about 4 g/day, preferably about 2 g/day.

The treatment normally lasts about 6 to 12 months, however, the length of treatment is decided by the skilled person, usually the family doctor or the doctor in charge.

By the term "about" it is intended a range around the indicated values, namely the lower and higher dosage, the length of the treatment and other parameters involved in the present invention. The person skilled in the art, by carrying out the invention, will use the normal, general experience in determining the range implied in the term "about". For example, the dosage can be adjusted around the indicated values depending on the patient's conditions, degree of the disease and any other element evaluated in the normal practice in this field.

Preferably, the medicament is in the form of a package suitable for oral treatment. This can be particularly advantageous for non-hospitalized, home-cared patients.

There is no particular or limiting indication on the kind of physical training, which can be combined with the administration of propionyl L-carnitine, or a pharmaceutically acceptable salt thereof, in the method according to the present invention.

The kind of physical training will be determined by the person skilled in the art, for example the medical doctor, depending on the severity of the intermittent claudication to be treated, the general conditions of the patient, other concomitant diseases, or any other factor which will be considered.

Some examples of physical training are:
3 times a day walking between about 1000 to 1500 m;
1-2 times a day walk for intervals 5-6 times over 80-100 m;
3 times daily 20-30 minutes hill walk;
Walking whole day;
0.5-2 hour daily walk;
2-8 km/day, v=2-4 km/h;
Walking program of 10 minutes/day;
Walking ½ mile 5 days/wk to the point of pain, then walking further;
Walks several times every day until point of pain or tightness;
Bicycles 10 km a day;
Exercise bike and/or stair climber;
Riding stationary bicycle—about 5 min at a time, 1-2 times daily;
Supervised exercise trainings programmes as administered in a rehabilitation facility;
Gymnastics 25× standing on toes home trainer;
Massages;
Hydrotherapy;
30 minutes total treadmill times 6-7×/wk;
Swims every day.

The following example further illustrates the invention.

EXAMPLE

Clinical Studies

Three parallel, randomized, double-blind, placebo-controlled, phase III studies in patients with Intermittent Claudication (Leriche-Fontaine Class II) represent the basis for the above considerations. They are study ST 261 201 90 INT (hereinafter referred to as the European study); study ST 94 301 (hereinafter referred to as the Hiatt study); and ST 93 301, hereinafter referred to as the Porter study).

Diagnosis and main criteria for inclusion for these studies were similar, as follows: intermittent claudication of ascertained vascular origin; age between 40 and 80 years; lesions at iliac-femoral and/or femoro-popliteal level confirmed by angiographic or Doppler examination; no pain at rest (Leriche-Fontaine Class III) or ulcerative lesions (Leriche-Fontaine Class IV); history of claudication >1 year; dietary regime and alcohol intake stable during the study. All patients were strongly encouraged to stop smoking and exercise actively. The latter recommendation was to be achieved either through a supervised, vascular rehabilitation-based program, or via an unsupervised, home-based program.

A total of 316 subjects (PLC, 153 subjects; placebo, 163 subjects) were randomized in the primary intention-to-treat population (ITT) of the European study, which was conducted in 39 centers in West and East Europe, and tested PLC (2 g/day) for 12 months vs. placebo. Patients had to have a maximum walking distance (MWD) at baseline between 50-400 m. and variability over the three treadmill tests carried-out at baseline of ≦25%.

A total of 161 subjects (PLC, 85 subjects; placebo, 76 subjects) were randomized in the ITT population of the Hiatt study, which was performed in 10 centers in the USA and Russia, and tested PLC (2 g/day for 6 months) versus placebo. All randomized subjects had a baseline peak walking time (PWT) between 60-300 sec (corresponding to about 50-250 m) and variability ≦20%.

A total of 155 subjects (ITT population: PLC, 80 subjects; placebo, 75 subjects) were randomized in the 6-month, Porter study, which was conducted in 16 US centers and tested PLC 2 g/day vs. placebo as its primary target population. All randomized patients had baseline MWD between 50-250 m and variability ≦25%.

These phase III studies evaluated physical performance as their primary efficacy parameter. This was assessed by the maximum walking capacity of patients on a treadmill: the European study used a fixed treadmill with 7% slope and 3 km/hour speed; the Hiatt study used a graded treadmill, starting at 0% slope and increasing by 2% every 2 minutes, with a 2 mph speed; the Porter study used a fixed treadmill with 12% slope and 2 mph speed. In order to make the results of these different treadmill protocols comparable, they were converted to a common slope (7%) and speed (3 km/h).

The above studies also assessed quality of life (QoL) as their main secondary efficacy parameter: the European study used the ad-hoc validated PAD-related questionnaire, while the Hiatt and Porter studies used both the very well-known and validated Health Status Survey-Short Form 36 (SF-36) and the Walking Impairment Questionnaire (WIQ).

Given the non-normality of response distributions for MWD, the comparison between PLC and placebo-treated patients was based on a non-parametric test, i.e., the Cochrane-Mantel-Haenszel test on the within-center, standardized mid-ranks (MODRIDITS) of changes over baseline, stratified by site.

Overall, the analysis for the 316 ITT subjects randomized in these three studies (PLC, 153 subjects; placebo, 163 subjects) showed a better exercise performance for PLC than placebo at endpoint (net PLC advantage=18.2 m, p=0.08). However, when only the ITT patients with concomitant physical exercise programs were considered, the results were in favour of the PLC treated subjects in a highly significant manner, as shown in Table 1.

TABLE 1

Changes in MWD (m) and PWT (sec) converted into MWD (m) on a treadmill with 7% slope and 3 km/h speed - ITT population with concomitant physical exercise

|  | PLC (N = 54) | Placebo (N = 49) |
|---|---|---|
| Baseline |  |  |
| Mean | 249.7 | 289.4 |
| SD | 112.6 | 130.5 |
| Median | 239.2 | 279.8 |
| Month 6/Endpoint |  |  |
| Mean | 410.8 | 358.7 |
| SD | 229.9 | 219.9 |
| Median | 400.9 | 299 |
| Change from Baseline to Endpoint |  |  |
| Mean | 161.1 | 69.3 |
| SD | 153.8 | 149.2 |
| Median | 154.8 | 27 |
| P-value | 0.000 |  |

Conversely, when the ITT patients without any form of concomitant physical exercise program were assessed, no difference was shown between the PLC and placebo groups, as shown in Table 2.

TABLE 2

Changes in MWD (m) and PWT (sec) converted into MWD (m) on a treadmill with 7% slope and 3 km/h speed - ITT population without concomitant physical exercise

|  | PLC (N = 264) | Placebo (N = 265) |
|---|---|---|
| Baseline |  |  |
| Mean | 205.6 | 203.0 |
| SD | 116.2 | 102.1 |
| Median | 171.7 | 161.9 |
| Month 6/Endpoint |  |  |
| Mean | 325.3 | 316.7 |
| SD | 293.2 | 292.7 |
| Median | 225.5 | 219.0 |

TABLE 2-continued

Changes in MWD (m) and PWT (sec) converted into MWD (m) on a treadmill with 7% slope and 3 km/h speed - ITT population without concomitant physical exercise

|  | PLC (N = 264) | Placebo (N = 265) |
|---|---|---|
| Change from Baseline to Endpoint |  |  |
| Mean | 119.7 | 115.8 |
| SD | 241.3 | 244.5 |
| Median | 36.6 | 36.3 |
| P-value | 0.777 |  |

The above results show that the concomitant undertaking of a physical training program is capable of boosting the beneficial effect of PLC administration.

Similar results were obtained also when considering QoL. Since several questionnaires were used in each study, a global summary statistic was used in order to deal with this issue, as well as with the multiplicity of domains present in each of these questionnaires, i.e., the O'Brien test.

Overall, the analysis for the ITT subjects showed a significant improvement at endpoint for the PLC group as compared to the placebo group ($p<0.001$). However, when only the ITT subjects with concomitant physical exercise programs were considered, the results were strikingly in favour of the PLC treated subjects, as shown in Table 3.

TABLE 3

Change in O'Brien scores for QoL questionnaires - ITT population with concomitant physical exercise

|  | PLC (N = 54) | Placebo (N = 48) |
|---|---|---|
| Change from Baseline to Endpoint |  |  |
| Mean | 0.56 | 0.43 |
| SD | 0.16 | 0.18 |
| Median | 0.54 | 0.42 |
| P-value | <0.001 |  |

Conversely, this finding was not confirmed in the ITT subjects without any concomitant physical exercise, as shown in Table 4.

TABLE 4

Change in O'Brien scores for QoL questionnaires - ITT population without concomitant physical exercise

|  | PLC (N = 261) | Placebo (N = 264) |
|---|---|---|
| Change from Baseline to Endpoint |  |  |
| Mean | 0.51 | 0.48 |
| SD | 0.17 | 0.18 |
| Median | 0.50 | 0.49 |
| P-value | 0.142 |  |

Therefore, the concomitant undertaking of a physical training program was able to improve also the patient subjective feeling of well-being as measured by several validated QoL questionnaires, both general (SF-36) and disease-specific (PAD-related questionnaire, WIQ).

As far as the industrial applicability of the present invention is concerned, the preparation for pharmaceutical compositions for oral, enteral or parenteral, such as intravenous infusion, is obtained by any conventional method generally known in the art, for example as provided in the European Pharmacopoeia or United States Pharmacopoeia.

Examples of compositions are the following:
(a) Composition for tablets
one tablet contains:

| Active ingredient | | |
|---|---|---|
| propionyl L-carnitine HCl | mg | 500 |
| Excipients | | |
| microcrystalline cellulose | mg | 54.0 |
| polyvinylpyrrolidone | mg | 18.0 |
| crospovidone | mg | 30.0 |
| magnesium stearate | mg | 15.0 |
| precipitated silica | mg | 3.0 |
| hydroxypropylmethylcellulose | mg | 10.0 |
| polyethyleneglycol 6000 | mg | 2.5 |
| titanium dioxide | mg | 1.8 |
| methacrylate copolymer | mg | 8.3 |
| purified talc | mg | 2.4 |

(b) Composition for intravenously injectable vials
one vial contains:

| Active ingredient | | |
|---|---|---|
| propionyl L-carnitine HCl | mg | 300 |
| Excipients | | |
| mannitol | mg | 300 |
| One vial of solvent contains: | | |
| sodium acetate•3H$_2$O | mg | 390 |
| water for injection q.s. to | ml | 5. |

The invention claimed is:

1. A method for treating a subject suffering from intermittent claudication (IC) wherein said subject takes an effective dose of propionyl L-carnitine or a pharmaceutically acceptable salt thereof and also engages in a concomitant physical training program selected from the group consisting of: 3 times a day walking between about 1000 to 1500 m; 1-2 times a day walk for intervals 5-6 times over 80-100 m; 3 times daily 20-30 minutes a hill walk; walking a whole day; 0.5-2 hour daily walk; 2-8 km/day, v=2-4 km/h; walking program of 10 minutes/day; walking ½ mile 5 days/wk to the point of pain, then walking further; walks several times every day until point of pain or tightness; bicycle 10 km a day; exercise bike and/or stair climber; riding a stationary bicycle-about 5 min at a time, 1-2 times daily; supervised exercise training programs as administered in a rehabilitation facility; gymnastics 25× standing on toes home trainer; massages; hydrotherapy; 30 minutes total treadmill times 6-7×/wk; and swim every day.

2. The method according to claim 1, wherein said salt of propionyl L-carnitine is selected from the group consisting of chloride, bromide, orotate, acid aspartate, acid citrate, magnesium citrate, acid phosphate, fumarate, acid fumarate, magnesium fumarate, lactate, maleate, acid maleate, mucate, acid oxalate, pamoate, acid pamoate, acid sulfate, glucose phosphate, tartrate, acid tartrate, magnesium tartrate, 2-amino ethansulfonate, magnesium 2-amino ethansulfonate, choline tartrate and trichloroacetate.

3. The method according to claim 1, wherein said intermittent claudication is at class II of the Lenche-Fontaine's classification.

4. The method according to claim 1, wherein said patient does not suffer from rest pain.

5. The method according to claim 1, wherein said propionyl L-carnitine is in the form of a package suitable for oral treatment.

6. The method according to claim 1, wherein said propionyl L-carnitine is given at a dose between about 1 g/day to about 4 g/day.

7. The method according to claim 1, wherein said treatment lasts about 6 to 12 months.

* * * * *